United States Patent [19]

Russell et al.

[11] Patent Number: 5,389,636
[45] Date of Patent: Feb. 14, 1995

[54] METHOD OF COMBATING VENTURIA

[75] Inventors: Philip E. Russell, Sawston, England; Heinz H. A. Hagemeister, Berlin, Germany

[73] Assignee: Schering Aktiengesellschaft, Berlin, Germany

[21] Appl. No.: 232,487

[22] Filed: Apr. 25, 1994

Related U.S. Application Data

[63] Continuation of Ser. No. 757,967, Sep. 12, 1991, abandoned.

[30] Foreign Application Priority Data

Sep. 15, 1990 [GB] United Kingdom ............... 9020207

[51] Int. Cl.$^6$ ............................................. A01N 43/54
[52] U.S. Cl. ................................................... 514/275
[58] Field of Search ......................................... 514/275

[56] References Cited

U.S. PATENT DOCUMENTS 4,992,438  2/1991  Ito et al. ................... 514/275

FOREIGN PATENT DOCUMENTS 0151404 10/1981 German Dem. Rep. ........... 514/275

Primary Examiner—Allen J. Robinson
Attorney, Agent, or Firm—Ostrolenk, Faber, Gerb & Soffen

[57] ABSTRACT

The fungal disease *Venturia*, especially *Venturia inaequalis*, can be combatted using 2-anilino-4,6-dimethylpyrimidine.

2 Claims, No Drawings

METHOD OF COMBATING VENTURIA

This is a continuation of application Ser. No. 07/757,967, filed Sep. 12, 1991, now abandoned.

This invention relates to an anilinopyrimidine compound having fungicidal activity.

In DDR Patent 151 404 there are described a group of anilinopyrimidine compounds having fungicidal activity. The species listed against which the compounds are said to be active are *Phytophthora infestans, Aspergillus niger, Botrytis cinerea, Erysiphe graminis* and *Rhizoctonia solani*. Test data are given for a number of compounds but for the chemically simplest compound exemplified in the patent, namely 2-anilino-4,6-dimethylpyrimidine, no biological activity is exemplified.

In EP 270 111, there are disclosed further anilinopyrimidines having fungicidal activity. Five test Examples are given in this patent application. In these Examples 2-anilino-4,6-dimethylpyrimidine is used as a comparison compound. The activities for the compounds of that application which are disclosed are *Botrytis cinerea, Alternaria brassicola, Pseudoperonospora cubensis, Pyricularia oryzae* and *Rhizoctonia solani*. In these examples 2-anilino-4,6-dimethylpyrimidine only showed significant activity against *Botrytis cinerea*. From this prior art, one would not expect 2-anilino-4,6-dimethylpyrimidine to have useful fungicidal activity except possibly against *Botrytis cinerea*. We have now surprisingly found that 2-anilino-4,6-dimethylpyrimidine has excellent activity against *Venturia* spp. and especially apple scab, *Venturia inaequalis*.

Thus according to the invention there is provided a method of combating *Venturia* spp., especially *Venturia inaequalis*, at a locus infested or liable to be infested therewith, which comprises applying 2-anilino-4,6-dimethylpyrimidine to that locus.

The invention also provides the use of 2-anilino-4,6-dimethylpyrimidine for combating Venturia spp., especially *Venturia inaequalis*.

The compound can be applied in conventional manner for applying fungicides to trees. It is generally formulated as a conventional agrochemical concentrate, which is diluted with water to the desired concentration prior to application. The concentrate usually comprises conventional surfactants and can be in the form for example of a suspension concentrate in water or a wettable powder.

The rate of application can vary over a wide range but the compound is usually applied at a concentration of 5 to 200 g active ingredient/hectolitre of spray, preferably 20 to 100 g/hectolitre.

The invention is illustrated in the following Example.

EXAMPLE 1

A wettable powder concentrate of 2-anilino-4,6-dimethylpyrimidine was diluted with water and then used to spray plots of apple trees infested with *Venturia inaequalis* at a rate of 40 g active ingredient per hectolitre of spray.

The test was carried out at two different sites in Germany. Both sites consisted of three replicate plots each comprising three trees. Trial 1 was sprayed nine times. Infection on the leaves was assessed 10 days after the eighth spray and infection on the fruit was assessed 7 weeks after the last spray. Trial 2 was sprayed seven times. Infection on the leaves was assessed 1 day after the last spray and infection on the fruit was assessed 8 weeks after the last spray. The results are as follows:

|  | % infection | |
|---|---|---|
|  | Leaves | Fruit |
| Site 1 | | |
| Compound of invention | 3.5 | 1.6 |
| Untreated | 18.4 | 87.7 |
| Site 2 | | |
| Compound of invention | 0.01 | 2.1 |
| Untreated | 20.0 | 48.0 |

It will be seen that 2-anilino-4,6-dimethylpyrimidine gives excellent control of *Venturia inaegualis*, compared with untreated trees.

EXAMPLE 2

A wettable powder concentrate of 2-anilino-4,6-dimethylpyrimidine was diluted with water and then used to spray plots of apple trees infested with *Venturia inaequalis* at rates of 30 and 40 g active ingredient per hectolitre of spray.

The test was carried out at a site in Belgium, which consisted of three replicate plots each comprising three trees. The trial was sprayed nine times. Infection on the leaves was assessed 7 days after the last spray. The results are as follows:

| Active ingredient | Concentration (% w/v) | % leaf infection |
|---|---|---|
| Compound of invention | 0.15 | 0.4 |
|  | 0.2 | 0.2 |
| Standards | | |
| dithianon[1] | 0.05 | 20.4 |
| metiram[2] | 0.2 | 15.6 |
| mancozeb[3] | 0.2 | 10.0 |
| captan[4] | 0.13 | 10.7 |
| Untreated |  | 81.3 |

[1] = 2,3-dicyano-1,4-dithiaanthraquinone
[2] = zinc ammoniate ethylenebis(dithiocarbamate) - poly(ethylenethiuram disulfide)
[3] = ethylenebis(dithiocarbamate) metal complex of copper and manganese
[4] = 1,2,3,6-tetrahydro-N-(trichloromethylthio)phthalimide It will be seen that 2-anilino-4,6-dimethylpyrimidine gives excellent control of *Venturia inaegualis*, compared with untreated trees and compared with the standards used at recommended rates for this disease.

We claim:

1. A method of combating a *Venturia* spp infestation in apple trees, which comprises applying an anti-*Venturia* effective amount of 2-anilino-4,6-dimethylpyrimidine to the apple trees.

2. The method claim 1 in which the *Venturia* spp is *Venturia inaequalis*.

* * * * *